(12) United States Patent
Maeda

(10) Patent No.: US 7,226,165 B2
(45) Date of Patent: Jun. 5, 2007

(54) OPHTHALMOLOGIC APPARATUS

(75) Inventor: Yasuo Maeda, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 226 days.

(21) Appl. No.: 10/968,988

(22) Filed: Oct. 21, 2004

(65) Prior Publication Data
US 2005/0105049 A1    May 19, 2005

(30) Foreign Application Priority Data
Nov. 17, 2003 (JP) .............................. 2003-386995

(51) Int. Cl.
*A61B 3/14* (2006.01)
(52) U.S. Cl. ...................... 351/208; 351/206
(58) Field of Classification Search ............... 351/206, 351/208, 200
See application file for complete search history.

(56) References Cited

U.S. PATENT DOCUMENTS

| 5,302,979 | A | | 4/1994 | Maeda et al. |
| 5,532,769 | A | | 7/1996 | Miwa et al. |
| 5,548,354 | A | * | 8/1996 | Kasahara et al. ........... 351/206 |
| 5,589,899 | A | | 12/1996 | Maeda et al. |
| 5,844,659 | A | * | 12/1998 | Isogai ........................ 351/208 |
| 5,889,576 | A | * | 3/1999 | Fujieda ....................... 351/208 |
| 2002/0159028 | A1 | * | 10/2002 | Masaki ....................... 351/200 |
| 2003/0097053 | A1 | | 5/2003 | Itoh |

FOREIGN PATENT DOCUMENTS

| JP | 8-10226 | 1/1996 |
| JP | 9-84760 | 3/1997 |
| JP | 2002-186585 | 7/2002 |

* cited by examiner

*Primary Examiner*—Scott J. Sugarman
(74) *Attorney, Agent, or Firm*—Fitzpatrick, Cella, Harper & Scinto

(57) ABSTRACT

There is provided an ophthalmologic apparatus which is easily operated. In the ophthalmologic apparatus, during measurement using an eye examination portion for measuring an optical characteristic of an eye to be examined, the eye examination portion is moved relative to the eye to be examined in up/down and left/right directions by manual input. Then, the eye examination portion is moved relative to the eye to be examined in a forward/backward direction by automatic control.

2 Claims, 9 Drawing Sheets

OPHTHALMOLOGIC APPARATUS

BACKGROUND OF THE INVENTION

1. Field of the Invention

The present invention relates to alignment of an ophthalmologic apparatus for measuring optical characteristics of an eye to be examined.

2. Related Background Art

According to an eye refractive power measuring apparatus serving as an ophthalmologic apparatus, which is described in Japanese Patent Application Laid-Open No. 2002-186585, an alignment reference index is set by projecting an alignment index light flux to an eye to be examined. The alignment between the eye to be examined and the refractive power measuring apparatus is performed using the reference index by so-called auto alignment for electrically driving an eye examination optical portion of the refractive power measuring apparatus relative to the eye to be examined in the left/right, up/down, and forward/backward directions.

In the ophthalmologic apparatus for performing the measurement through such auto alignment, the measurement is always performed on the eye to be examined at the same location thereof. For example, assume that the eye to be examined has opacity resulting from cataract at the central region of the crystalline lens. In this case, even if measurement is tried multiple times, the measurement on the central region including the opacity is repeated by the auto alignment. Therefore, a measurement light flux is blocked by the opacity, so that the measurement light flux cannot be detected. As a result, there is a problem in that the measurement is not completed because a measurement error is repeated.

In addition to such an auto alignment function for performing the alignment measurement, the ophthalmologic apparatus has the same manual measurement function as that of a conventional eye examination apparatus. In the manual measurement function, an operator operates the eye examination optical portion in the left/right, up/down, and forward/backward directions to move the eye examination optical portion to a desirable position. The alignment measurement is performed at the position.

However, when the alignment measurement is manually performed, it is necessary for the operator to operate the eye examination optical portion taking into consideration not only left/right and up/down alignments but also forward/backward alignment (that is, focusing). Thus, the usability of the ophthalmologic apparatus having the auto alignment function impairs under the current circumstances.

SUMMARY OF THE INVENTION

An object of the present invention is to provide an ophthalmologic apparatus that is easy to operate.

In order to achieve the above object, for example, an ophthalmologic apparatus of the present invention comprises the following arrangement.

That is, an ophthalmologic apparatus according to the present invention includes:

eye examination means for examining an eye to be examined;

input means for inputting moving amounts of the eye examination means in up/down and left/right directions, with respect to the eye to be examined;

first drive means for moving the eye examination means in up/down and left/right directions in accordance with the input moving amounts;

detection means for detecting a distance in forward/backward direction between the eye examination means and the eye to be examined;

second drive means for moving the eye examination means in forward/backward direction; and control means for controlling the second drive means, while the first moving means acts, so as to make appropriately the distance in forward/backward direction between the eye examination means and the eye to be examined.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

Figure 1:
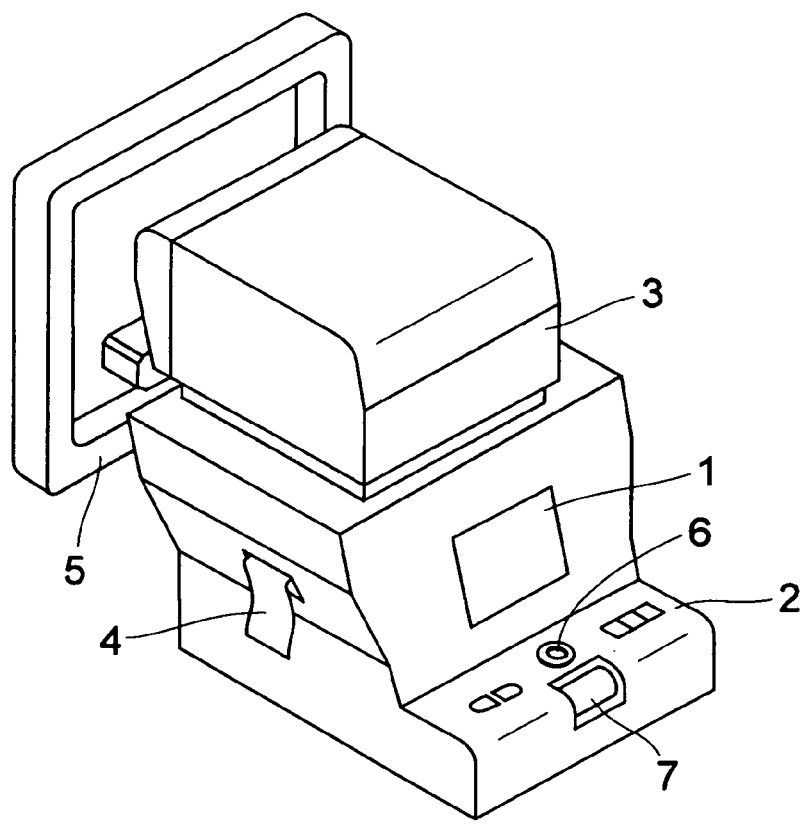
FIG. 1 is an external view showing an eye refractive power measuring apparatus according to an embodiment of the present invention.

FIG. 1 is an external view showing an eye refractive power measuring apparatus, i.e., an ophthalmologic apparatus for measuring an eye refractive power of an eye to be examined according to an embodiment of the present invention. The front surface of the eye refractive power measuring apparatus is an operational surface operated by an operator. A display portion 1 for displaying a measurement value obtained by measurement and an image of the eye to be examined and a switch panel 2 are located on the operational surface. The display portion 1 is composed of a CRT monitor or a liquid crystal monitor. A movable measurement portion 3 is located in an upper part of the eye refractive power measuring apparatus and a printer 4 for printing a result obtained by measurement and the like is located on a side surface thereof. A chin support portion 5 for a person to be examined is provided on an opposite side of the operational surface.

Figure 2:
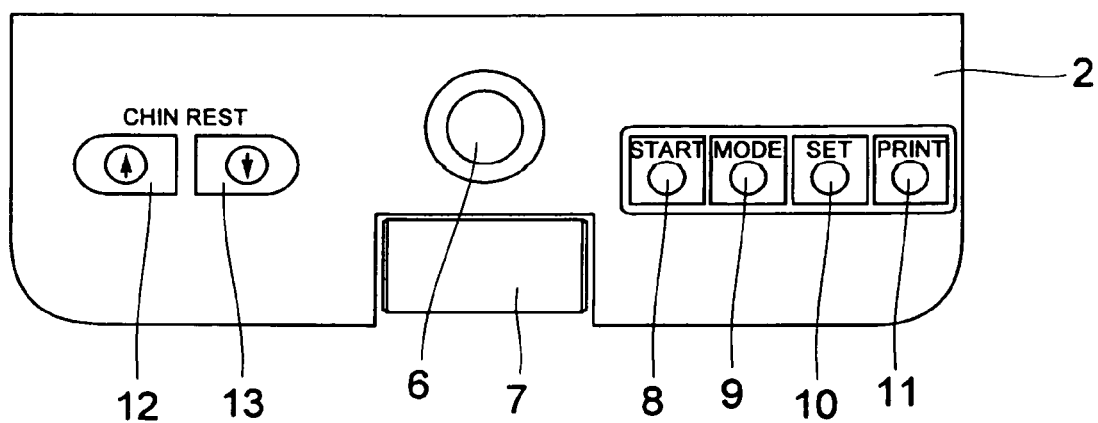
FIG. 2 is a plan view showing an operational panel.

FIG. 2 is a plan view showing the switch panel 2. The switch panel 2 includes a trackball 6, a roller 7, a measurement start switch 8, a measurement mode select switch 9, a set switch 10, and a print switch 11. The trackball is used for moving the measurement portion 3 relative to the eye to be examined in the up/down and left/right directions. The roller 7 is connected with a rotary encoder for moving the measurement portion 3 relative to the eye to be examined in the forward/backward direction. The measurement start switch 8 is used for starting auto alignment and measurement with the eye to be examined. The measurement mode select switch 9 is used for selecting a mode of automatically measuring the eye refractive power of the eye to be examined (auto alignment mode) or a mode of measuring the eye refractive power of the eye to be examined with manual alignment using the trackball 6 and the roller 7 (manual mode). The set switch 10 is used for performing various apparatus settings such as a distance between vertex cornea for eye refractive power measurement, a sign of an astigmatic power, and a display unit thereof. The print switch 11 is used for causing the printer 4 to print a result obtained by measurement. The switch panel 2 further includes a switch 12 for moving the chin support portion 5 upward by a chin support portion up/down motor and a switch 13 for moving the chin support portion 5 downward thereby.

Figure 3:
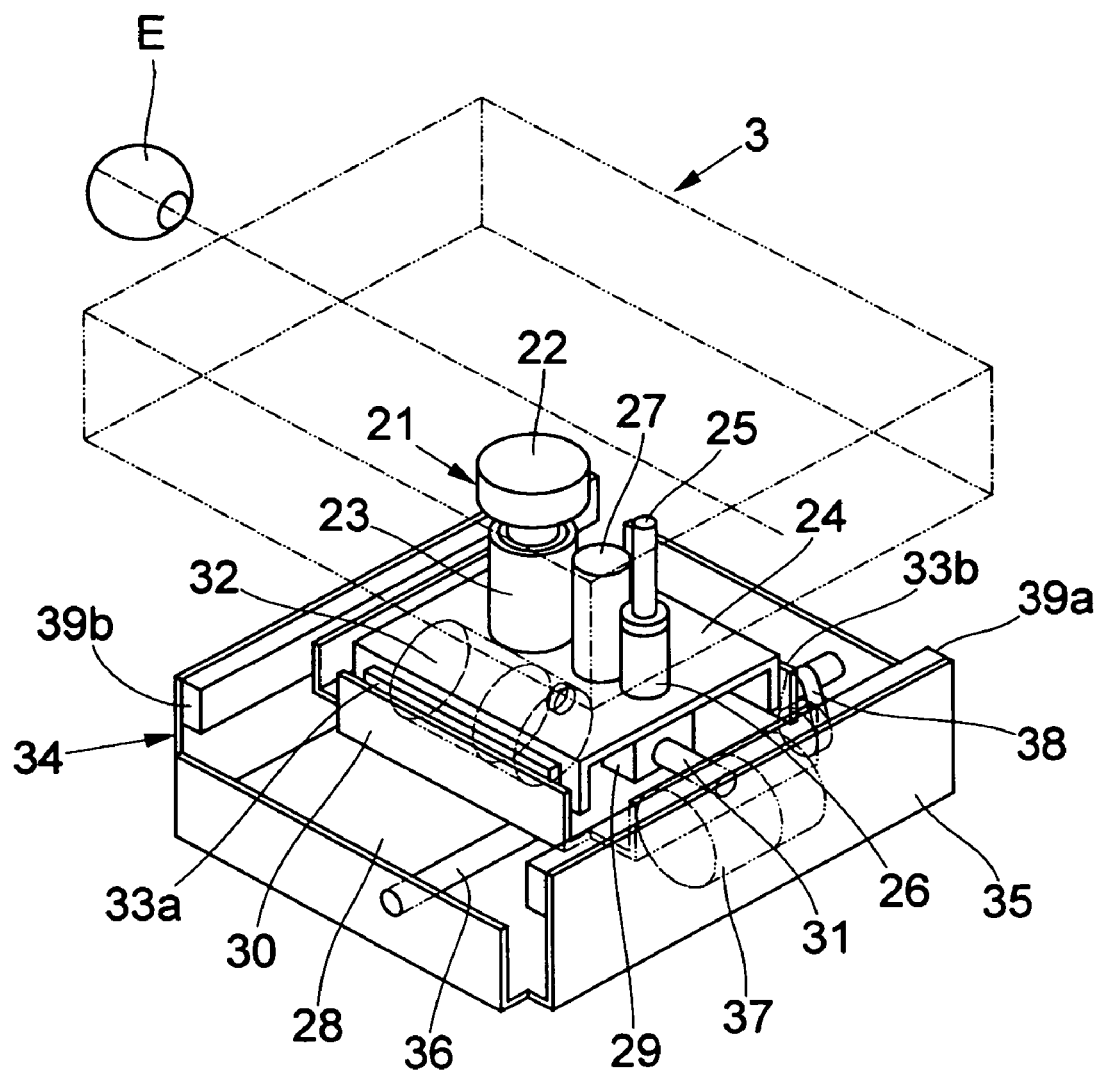
FIG. 3 is an explanatory view showing a drive mechanism of a measurement portion.

FIG. 3 is an explanatory view showing a mechanism for driving the measurement portion 3 relative to an eye to be examined E in the forward/backward, left/right, and up/down directions, in order to align the measurement optical axis of the measurement portion 3 with the eye to be examined E. The measurement portion 3 is connected with an up/down drive portion 21 and can be driven in a range of about 30 mm in the up/down direction by the up/down drive portion 21.

The measurement portion 3 is supported on an up/down support 22 which is connected with an up/down drive support 23 that contains a direct-drive ball bearing and an up-and-down feed screw. The up/down drive support 23 is fixed onto an up/down drive base 24. In order to regulate the rotation of the up/down support 22 of the measurement portion 3 about the central axis, a detent support 25 protrudes from the measurement portion 3 upward. The detent support 25 is fixed onto the up/down drive base 24 and engaged with a direct-drive bearing 26.

An up/down motor 27 for up/down driving is located between the up/down drive support 23 and the direct-drive bearing 26. The feed screw of the up/down drive support 23 can be rotated by the up/down motor 27 through a belt provided on the rear surface of the up/down drive base 24. Therefore, the measurement portion 3 can be moved upward and downward by the forward and reverse rotations of the up/down motor 27.

Although not shown, both ends of a stroke of 30 mm in the up/down direction can be detected for movement limit positions by limit switches. A pulse counting encoder is located concentric with the output shaft of the up/down motor 27. A photo coupler for detecting an output of the encoder is provided on the rear surface of the up/down drive base 24.

A female screw nut 29 is fixed onto the rear surface of the up/down drive base 24 driven by the forward/backward drive portion 28. The female screw is threaded into a feed screw 31 supported by a forward/backward drive base 30. The feed screw 31 is connected with a forward/backward motor 32 through coupling. Direct-drive guide rails 33a and 33b are located on both left/right side surfaces of the up/down drive base 24. A movable side of the rails is connected with the up/down drive base 24 and a fixed side of the rails is connected with the forward/backward drive base 30.

According to the forward and reverse rotations of the forward/backward motor 32, the measurement portion 3 including the up/down drive portion 21 can be moved in the forward/backward direction. Although not shown, both ends of a stroke of 40 mm in the forward/backward direction can be detected for movement limit positions by limit switches similarly to the up/down drive portion. A pulse counting encoder is located concentric with the shaft of the forward/backward motor 32. A photo coupler for detecting an output of the encoder is located on the upper surface of the forward/backward drive base 30.

In a left/right drive portion 34 for driving the forward/backward drive base 30 in the left/right direction, as in the forward/backward drive portion 28, a female screw nut which is not shown is fixed onto the rear surface of the forward/backward drive base 30. The female screw is threaded into a feed screw 36 supported by a left/right drive base 35. The feed screw 36 is connected with a left/right motor 37 through a belt 38. Direct-drive guide rails 39a and 39b are located on both forward/backward side surfaces of the forward/backward drive base 30. A movable side of the rails is connected with the forward/backward drive base 30 and a fixed side of the rails is connected with the left/right drive base 35.

According to the forward and reverse rotations of the left/right motor 37, the measurement portion 3 including the up/down drive portion 21 and the forward/backward drive portion 28 can be moved in the left/right direction. Although not shown, as in the case of the forward/backward drive portion 28, both ends of a stroke of 90 mm in the left/right direction can be detected for movement limit positions by limit switches. A pulse counting encoder is located concentric with the shaft of the left/right motor 37. A photo coupler for detecting an output of the encoder is located on the upper surface of the left/right drive base 35.

Therefore, the measurement portion 3 can be moved relative to the eye to be examined E in the three-dimensional directions by the up/down drive portion 21, the forward/backward drive portion 28, and the left/right drive portion 34. Thus, the alignment can be performed by electrical driving with a state in which the chin of any of persons of all ages is supported on the chin support portion 5.

Figure 4:
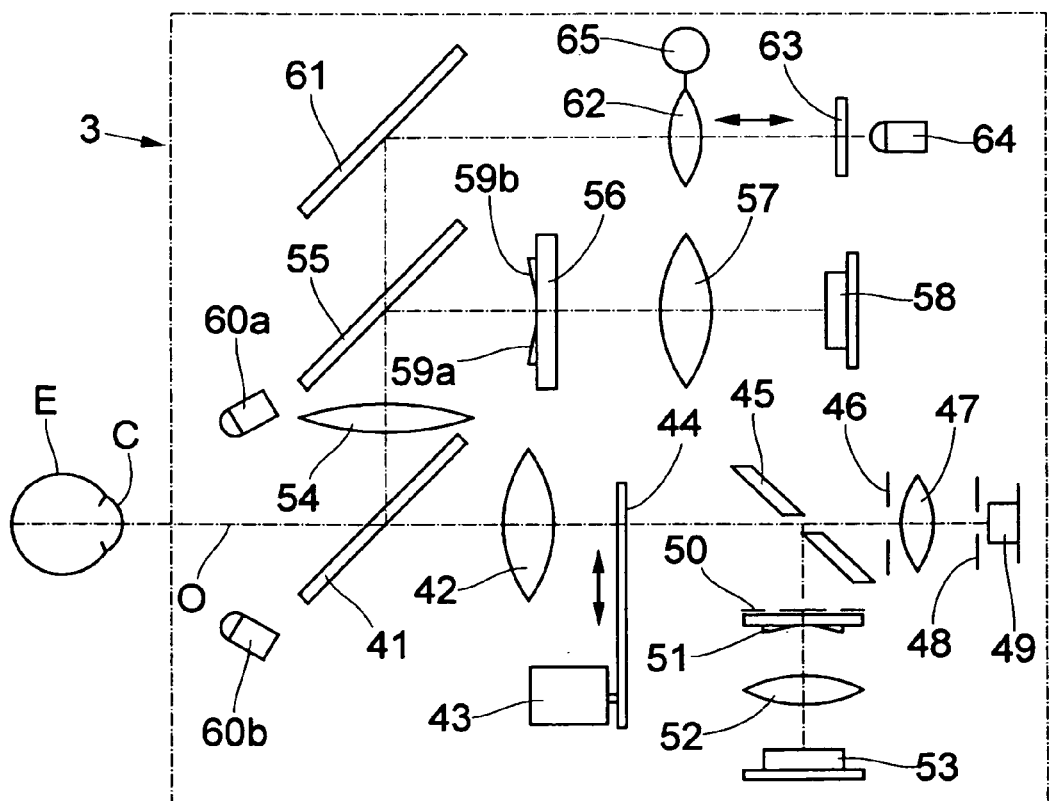
FIG. 4 is an optical structural view showing the measurement portion.
Figure 5:
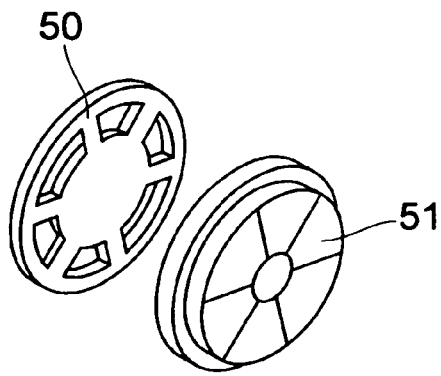
FIG. 5 is a perspective view showing a six-part diaphragm and a six-part prism.

FIG. 4 is an arrangement view showing an optical system included in the measurement portion 3. A dichroic mirror 41, an objective lens 42, a diffusion plate 44, a holed mirror 45, a diaphragm 46, a projection lens 47, a projection diaphragm 48, and a measurement light source 49 are disposed in order from the side of the eye to be examined E on a central axis O of the measurement portion 3 aligned with the optical axis of the eye to be examined. The dichroic mirror 41 is used for totally reflecting visible light and partially reflecting a light flux having a wavelength of 880 nm. The diffusion plate 44 is driven by a diffusion plate motor 43. The measurement light source 49 emits the light flux having the wavelength of 880 nm. A six-part diaphragm 50, a six-part prism 51, a light receiving lens 52, and a two-dimensional image pickup element 53 are disposed in order in the light reflecting direction of the holed mirror 45. The six-part diaphragm 50 and the six-part prism 51 each have a shape shown in FIG. 5 and are actually in contact with each other.

The above-mentioned optical system is used for eye refraction measurement. A light flux emitted from the measurement light source 49 is limited by the projection diaphragm 48 and primarily imaged in front of the objective lens 42 by the projection lens 47. Then, the light flux passes through the objective lens 42 and the dichroic mirror 41 and is projected to the center of pupil of the eye to be examined E. The light flux is imaged onto the eye fundus. A reflected light flux on the eye fundus passes through the vicinity of pupil and is incident on the objective lens 42 again. The incident light flux passes through the objective lens 42 and then is reflected on the peripheral portion of the holed mirror 45.

The reflected light flux is pupil-split by the six-part diaphragm 50 substantially conjugate with the pupil of the eye to be examined. The split light fluxes are projected as six spot images onto the light receiving surface of the two-dimensional image pickup element 53 by the six-part prism 51. When the eye to be examined E is an emmetropia, an approximate curve connecting the barycenters of the six spot images becomes a predetermined circle. When the eye to be examined E is a shortsighted eye or a longsighted eye, a curvature of the circle of the approximate curve increases or decreases. When the eye to be examined E is astigmatic, the approximate curve becomes an ellipse. An angle formed by the horizontal axis and the longitudinal axis of the ellipse becomes an astigmatic axial angle. A refractive value is calculated based on coefficients of the elliptic approximate curve.

A fixation projection optical system and an alignment light receiving optical system used for both anterior segment observation of the eye to be examined and alignment detection are disposed in the light reflecting direction of the dichroic mirror 41. The alignment light receiving optical system includes a lens 54, a dichroic mirror 55, an alignment prism diaphragm 56, an imaging lens 57, and a two-dimensional image pickup element 58, which are disposed from the dichroic mirror 41 side.

Figure 6:
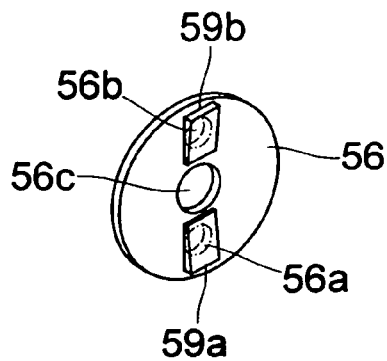
FIG. 6 is a perspective view showing an alignment prism diaphragm.

FIG. 6 shows a shape of the alignment prism diaphragm 56. Three opening portions 56a, 56b, and 56c provided in a disk-shaped diaphragm plate. Alignment prisms 59a and 59b transmitting only a light flux having a wavelength of around 880 nm are bonded to the dichroic mirror 55 side of each of the opening portions 56a, 56b located on both the sides of the opening portion 56c.

Anterior illumination light sources 60a and 60b for emitting light fluxes each having a wavelength of about 780 nm are disposed oblique to the front of the anterior segment of the eye to be examined E. The anterior segment of the eye to be examined E is illuminated by the anterior illumination light sources 60a and 60b. A light flux related to an image of the anterior segment is imaged onto the light receiving sensor surface of the two-dimensional image pickup element 58 through the objective lens 42, the dichroic mirror 41, the lens 54, the dichroic mirror 55, the central opening portion 56c of the alignment prism diaphragm 56, and the imaging lens 57. The measurement light source 49 for eye refractive measurement also serves as a light source for alignment detection. In alignment, the diffusion plate 44 which is semitransparent is inserted onto an optical path by the diffusion plate motor 43.

A position to which the diffusion plate 44 is inserted is a primary imaging position of a light flux from the measurement light source 49, which is imaged by the imaging lens 47. In addition to this, the diffusion plate 44 is inserted to the focal position of the objective lens 42. Therefore, the image related to the measurement light source 49 is temporarily formed on the diffusion plate 44. Therefore, the image becomes a secondary light source and is projected as thick parallel light flux from the objective lens 42 to the eye to be examined E.

The parallel light flux is reflected on a cornea C of the eye to be examined to form a bright spot image. The light flux passes through the objective lens 42 of the measurement portion 3 again and a part of the light flux is reflected on the dichroic mirror 41. The part of the light flux is reflected on the dichroic mirror 55 through the lens 54 and passes through the opening portion 56c of the alignment prism diaphragm 56 and the alignment prisms 59a and 59b. Then, the part of the light flux is converged by the imaging lens 57 and imaged onto the image pickup surface of the two-dimensional image pickup element 58.

The central opening portion 56c of the alignment prism diaphragm 56 transmits the light fluxes each having the wavelength of 780 nm or more, which are emitted from the anterior illumination light sources 60a and 60b. Therefore, as in the optical path of the reflected light flux on the cornea C, the reflection light flux related to the image of the anterior segment illuminated by the anterior illumination light sources 60a and 60b travels along an observation optical system. Then, the light flux is imaged to the two-dimensional image pickup element 58 by the imaging lens 57 through the opening portion 56c of the alignment prism diaphragm 56. A light flux having passed through the alignment prism 59a is refracted downward and a light flux having passed through the alignment prism 59b is refracted upward.

The fixation projection optical system is located on the transmission side of the dichroic mirror 55. The fixation projection optical system includes a reflection mirror 61, a fixation guide lens 62, a fixation chart 63, and a fixation projection light source 64, which are disposed in order. In fixation guide, the fixation chart 63 is illuminated from the rear side with a projection light flux from the fixation projection light source 64 which is turned on. The light flux is projected to the fundus of the eye to be examined E through the fixation guide lens 62 and the lens 54. In order to realize a fogging state by diopter guide of the eye to be examined E, the fixation guide lens 62 can be moved in the optical axial direction by a fixation guide motor 65.

Figure 7:
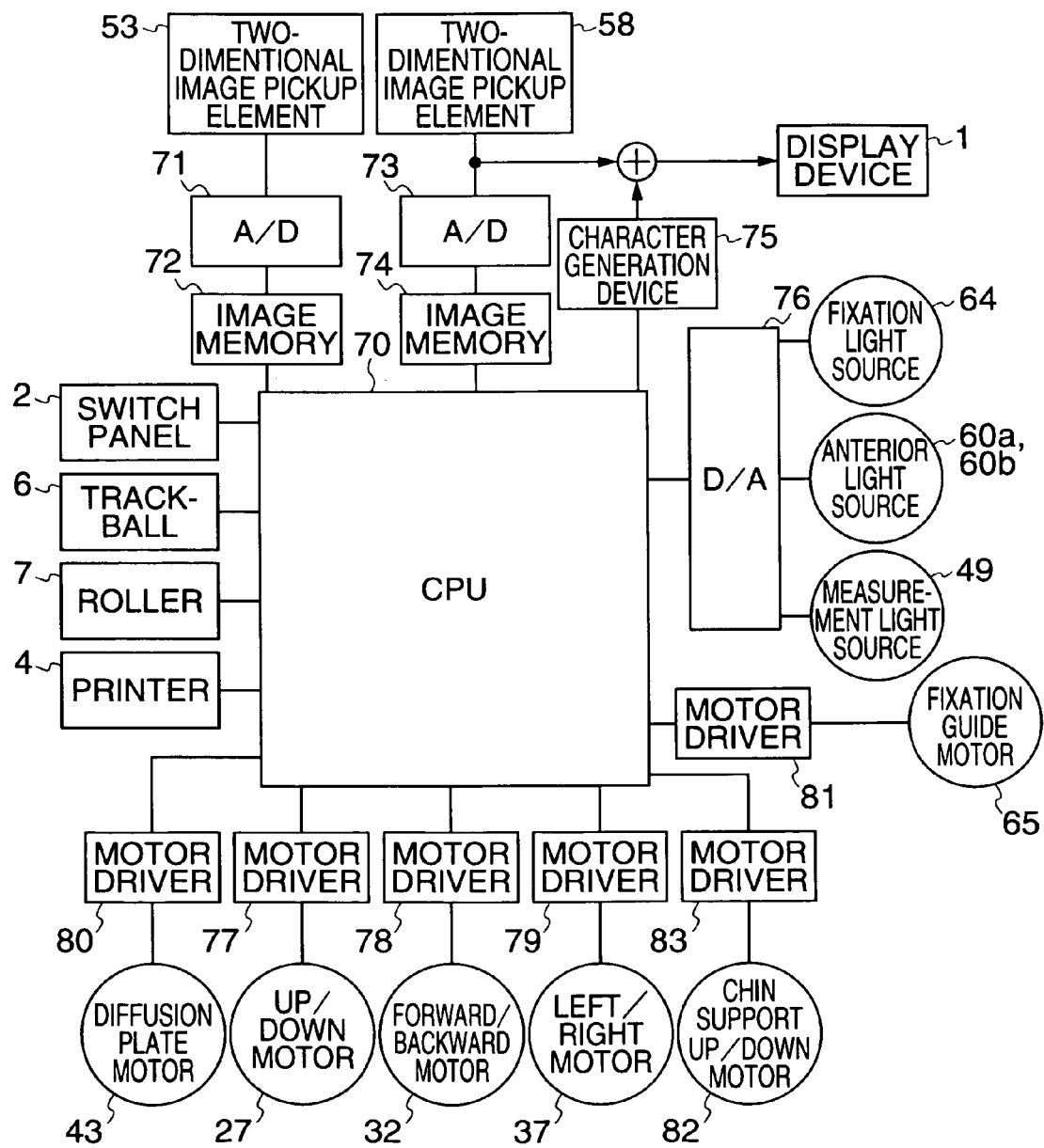
FIG. 7 is a block circuit diagram showing the eye refractive power measuring apparatus.

FIG. 7 is a block circuit diagram showing the eye refractive power measuring apparatus. The switch panel 2 which includes the measurement start switch and the print start switch and the printer 4 are connected with ports of a CPU 70.

A video signal of the eye fundus image taken by the two-dimensional image pickup element 53 is converted into digital data by an A/D converter 71 and stored in an image memory 72. The CPU 70 calculates an eye refractive power based on the image stored in the image memory 72. A video signal of the anterior segment image taken by the two-dimensional image pickup element 58 is converted into digital data by an A/D converter 73 and stored in an image memory 74. The CPU 70 performs determination of an alignment state based on detected alignment bright spots and calculation of a curvature radius of the cornea of the eye to be examined, with reference to the image stored in the image memory 74.

The video signal of the anterior segment image taken by the two-dimensional image pickup element 58 is combined with a signal from a character generation device 75, and the anterior segment image, measurement values, and the like are displayed on the display portion 1. The measurement light source 49, the anterior illumination light sources 60a and 60b, and the fixation projection light source 64 are connected with a D/A converter 76 through drivers which are not shown. The amount of light from each of the light sources can be changed according to an instruction from the CPU 70.

The up/down motor 27, a forward/backward motor 32, the left/right motor 37, the diffusion plate motor 43, and the fixation guide motor 65 are driven according to instructions from the CPU 70 through corresponding motor drivers 77, 78, 79, 80, and 81. A drive motor (chin support up/down motor) 82 for driving the chin support portion 5 is connected with the CPU 70 through a motor driver 83. When any of the chin support up/down switches 12 and 13 of the switch panel 2 is pressed, the drive motor 82 is driven according to an instruction from the CPU 70.

Figure 8:
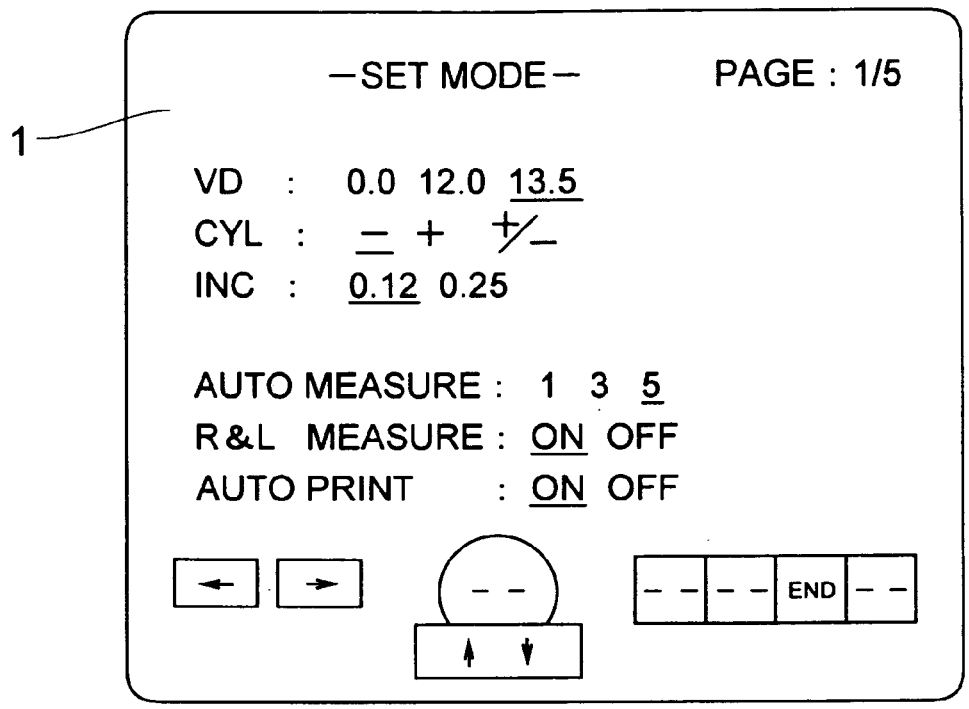
FIG. 8 is an explanatory view showing a set mode screen.

FIG. 8 shows a part of contents displayed on the screen of the display portion 1 to perform apparatus settings after the set switch 10 of the switch panel 2 is pressed. A distance between vertex cornea VD can be selected from 0, 12.0, and 13.5. A sign CYL of an astigmatic power can be selected from −, +, and +/−. A display unit INC can be selected from 0.12 and 0.25.

In the measurement through the auto alignment, "Auto Measure" related to the number of measurements per measurement point can be selected from 1, 3, and 5. "R&L Measure" for successively measuring the right and left eyes of a person to be examined through the auto alignment can be selected from a continuous measurement mode (ON) or a mode for performing only measurement of one eye (OFF). "Auto Print" for determining whether or not a result obtained by the measurement is automatically printed by the printer 4 after the completion of the measurement can be selected from ON and OFF.

In FIG. 8, underlined items of respective items indicate current settings. As shown in lowermost graphics, the settings can be instructed and changed by operating the trackball 6, the roller 7, the respective switches 8 to 11, and the chin support up/down switches 12 and 13.

In the measurement of the eye to be examined E, the person to be examined places his/her chin on the chin support portion 5 and puts his/her forehead to a forehead pad, thereby securing his/her face in position. In order to align the optical axis O of the measurement portion 3 with the eye to be examined E, an operator operates the trackball 6 and the roller 7. According to the operation of the trackball 6, the measurement portion 3 is moved relative to the eye to be examined E in the left/right and up/down directions. According to the operation of the roller 7, the measurement portion 3 is moved in the forward/backward direction. Therefore, the alignment of the measurement portion 3 can be performed.

According to such operations, the CPU 70 receives an output signal from a pulse counter connected with the trackball 6 and an output signal from the rotary encoder connected with the roller 7. Therefore, the amount of operation and speed of the eye refractive power measuring apparatus can be detected. The up/down motor 27, the forward/backward motor 32, and the left/right motor 37 are driven through the respective motor drivers 77, 78, and 79 based on the amount of operation and the speed.

The operator conducts the above-mentioned operations to move the measurement portion 3 while observing the anterior segment of the eye to be examined E using the display portion 1. When the pupil of the eye to be examined E is observed, the measurement start switch 8 of the switch panel 2 is pressed. Then, the eye refractive power measuring apparatus first starts the following auto alignment for automatically aligning the measurement portion 3 with the eye to be examined E.

(Auto Alignment)

Figure 9:
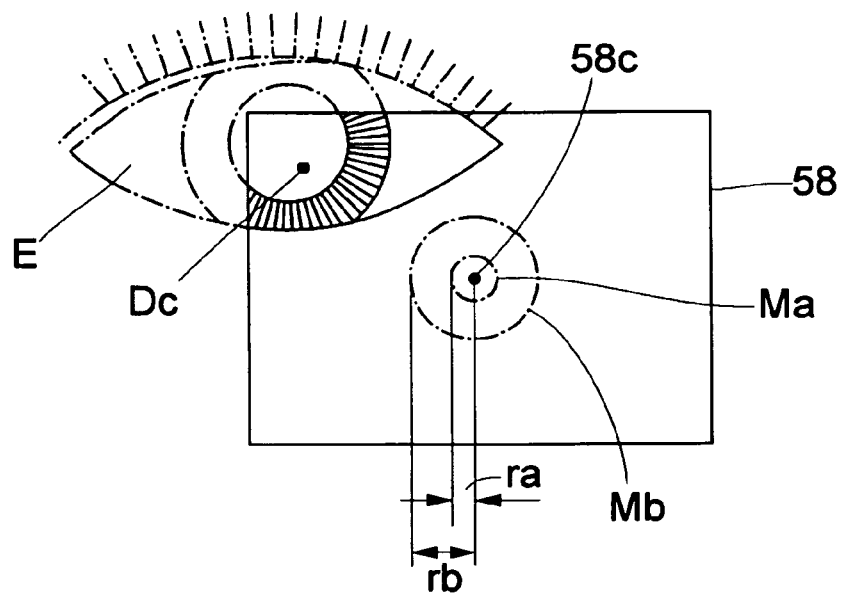
FIG. 9 is an explanatory view showing an anterior segment image.

FIG. 9 shows the anterior segment image of the eye to be examined E, which is taken by the two-dimensional image pickup element 58 at the measurement start time after the operator operates the trackball 6 and the roller 7. The CPU 70 causes the image memory 74 to temporarily store the anterior segment image and calculates an area center Dc of a dark region in the image. In this embodiment, for example, when the resolution of a pixel in the memory is set to 8 bits (256 levels), a threshold level is set to 80. A region darker than the threshold level is detected as a pupil region of the eye to be examined and the area center Dc of the dark region is calculated.

As shown in FIG. 9, when only a part of the pupil of the eye to be examined is picked up, the area center Dc does not coincide with the center of pupil. However, as described later, when the measurement portion 3 is moved to the center by the auto alignment function, an image of the entire pupil of the eye to be examined E is picked up. Therefore, even when the center of pupil and the area center Dc do not coincide with each other at the auto alignment start time, a problem does not occur.

The CPU 70 operates the up/down motor 27 and the left/right motor 37 such that the calculated area center DC of the pupil image coincides with a center 58c of the two-dimensional image pickup element 58 or falls within an alignment allowable area Ma, thereby moving the measurement portion 3 in the up/down and left/right directions. In the case as shown in FIG. 9, the area center DC of the pupil image of the eye to be examined E is positioned at the diagonally forward left of the center 58c. Therefore, the CPU 70 causes the motors 27 and 37 to be driven so as to move the measurement portion 3 in the up and right directions as viewed from the eye to be examined E.

The final alignment allowable area Ma is indicated by a radius ra. A target alignment allowable area Mb for rough alignment is indicated by a radius rb. The CPU 70 performs the above-mentioned calculation of the area center Dc of the pupil and calculations of a displacement direction and the amount of displacement with the center 58c. Then, the CPU 70 causes the measurement portion 3 to be driven until the calculated amount of displacement becomes equal to or smaller than the radius rb of a predetermined rough alignment allowable area. That is, the rough alignment operation between the central axis O of the measurement portion 3 and the eye to be examined E is continued.

Figure 10:
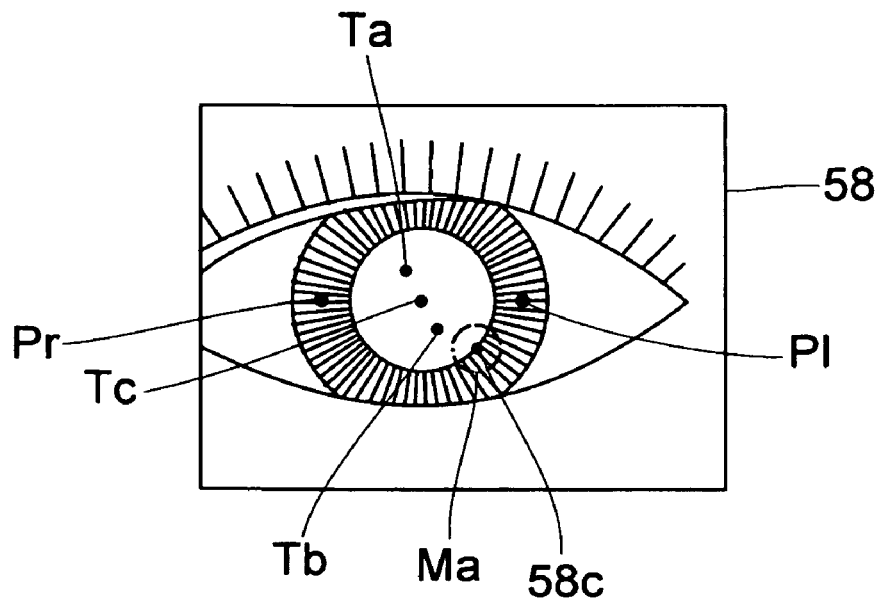
FIG. 10 is an explanatory view showing an anterior segment image.

When the area center Dc of the pupil falls within the target alignment allowable area Mb for rough alignment and thus a distance between the area center Dc and the center 58c is equal to or shorter than the radius rb, the CPU 70 causes the diffusion plate 44 to be inserted onto the optical path and causes the measurement light source 49 to turn on. FIG. 10 shows the anterior segment image at this time.

As described above, the light flux from the measurement light source 49 is temporarily imaged onto the diffusion plate 44 to form the image related to the measurement light source 49. Diffusion light fluxes related to the image are projected as parallel light fluxes to the cornea C of the eye to be examined E. The parallel light fluxes are reflected on the cornea C and imaged as a bright spot at position corresponding to ½ of the curvature radius of the cornea C as well known.

Three cornea bright spot images, that is, bright spots Ta, Tb, and Tc are projected onto the two-dimensional image pickup element 58 by the opening portions 56a, 56b, and 56c and the alignment prisms 59a and 59b in the alignment prism diaphragm 56 provided in the measurement portion 3. Bright spots Pr and Pl located on both sides of the bright spots indicate cornea reflection bright spots from the anterior illumination light sources 60a and 60b, which are caused by cornea reflection. The CPU 70 causes the image memory 74 to store the anterior segment image shown in FIG. 10 and detects the three bright spots Ta, Tb, and Tc.

Figure 11:
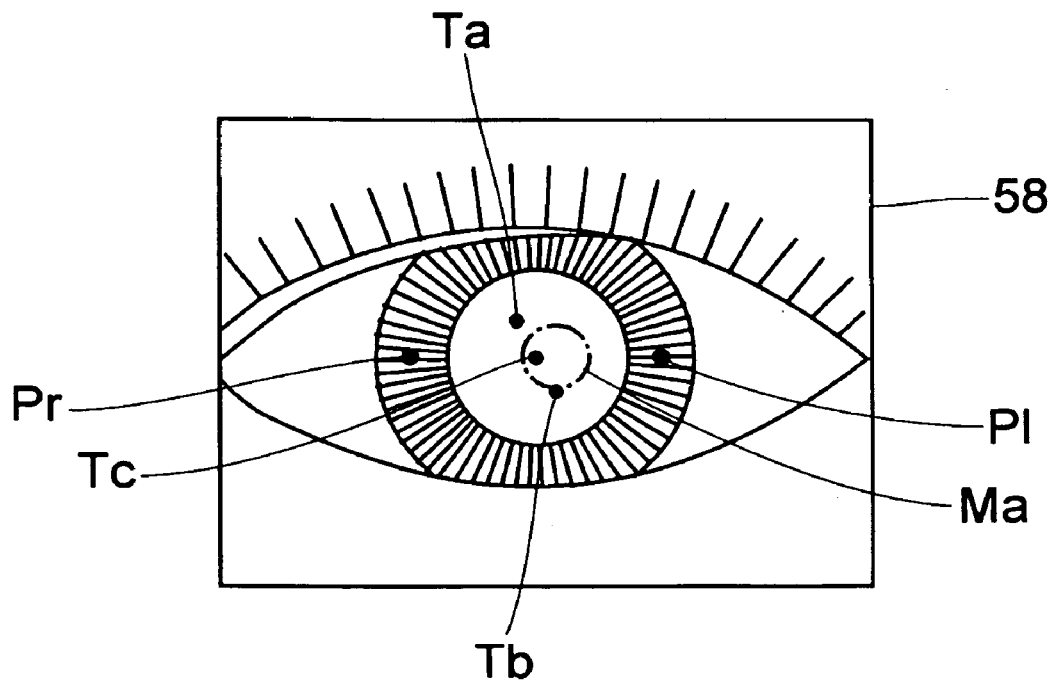
FIG. 11 is an explanatory view showing an anterior segment image.

When the three bright spots Ta, Tb, and Tc are detected, the measurement portion 3 is moved such that the central bright spot Tc is made to coincide with the center 58c. The CPU 70 causes the measurement portion 3 to move in the up/down and left/right directions as shown in FIG. 11 until the bright spot Tc falls within the final alignment allowable area Ma and thus a distance between the bright spot Tc and the center 58c becomes equal to or shorter than the radius ra. After that, the CPU 70 causes the measurement portion 3 to move in the forward/backward direction, thereby performing alignment in the focusing direction.

Figure 12:
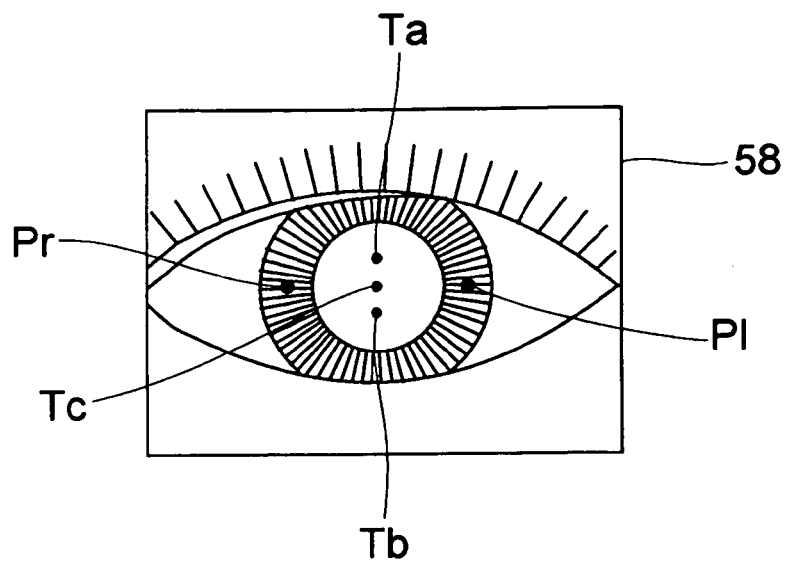
FIG. 12 is an explanatory view showing an anterior segment image.

The CPU 70 causes the measurement portion 3 to move in the forward/backward direction so as to align the cornea bright spots Ta and Tb with the bright spot Tc in the vertical direction. When the three cornea bright spots Ta, Tb, and Tc are aligned in line in the up/down direction as shown in FIG. 12, the alignment is completed.

A method of calculating a movement distance from a positional relationship among the three bright spots Ta, Tb, and Tc, that is, the behavior of the cornea bright spots Ta and Tb and the forward/backward moving direction of the measurement portion 3 are described in Japanese Patent Application Laid-Open No. H09-084760.

Figure 13:
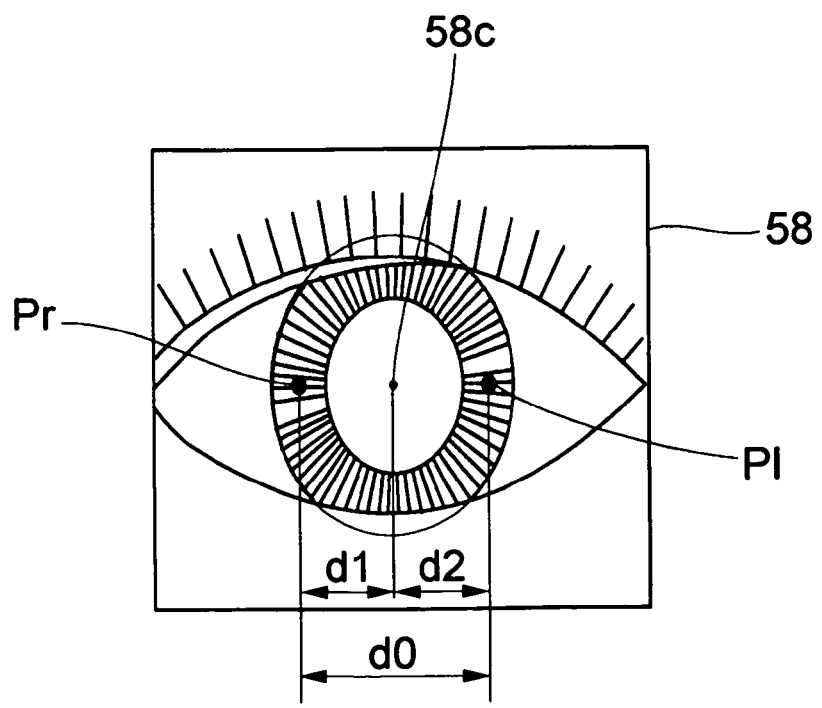
FIG. 13 is an explanatory view showing an anterior segment image.

After the completion of the alignment, the measurement light source 49 is temporarily turned off. Then, with a state shown in FIG. 13, intervals d0, d1, and d2 between the cornea reflection bright spots Pr and Pl resulting from the anterior illumination light sources 60a and 60b are measured and stored. In order to obtain the interval d1, a bright spot group is detected by scanning from the center 58c of the two-dimensional image pickup element 58 to the left and the barycenter of the bright spot group is calculated. Similarly, in order to obtain the interval d2, a bright spot group is detected by scanning from the center 58c to the right and the barycenter of the bright spot group is calculated. The interval d0 can be calculated as a distance between the barycenters of the cornea reflection bright spots Pr and Pl in the horizontal direction. As described later, when the measurement portion 3 is moved in the up/down and left/right directions, focusing in the forward/backward direction is performed based on the interval d0. Therefore, the intervals d0, d1, and d2 upon the completion of the alignment are required. Subsequently, the operation is shifted to refractive power measurement.

(Refractive Power Measurement)

In order to calculate a refractive power, the CPU 70 causes the diffusion plate 44 which is being inserted onto the optical path for the auto alignment to retract from the optical path. The measurement light source 49 which is being turned off is turned on to project the measurement light flux to the fundus of the eye to be examined E. Reflected light on the eye fundus travels along the above-mentioned optical path and is received in the two-dimensional image pickup element 53. An eye fundus image projected to the two-dimensional image pickup element 53 is divided into six spots by the refractive power of the eye to be examined. The six spot images are converted into digital data by the A/D converter 71 and stored in the image memory 72.

Respective barycentric coordinates of the six spot images stored in the image memory 72 are calculated and an equation of an ellipse passing through the six spots is obtained by a known method. The major length and minor length of the ellipse and a tilt of the major axis thereof are calculated to obtain the eye refractive power of the eye to be examined E. Note that eye refractive power values corresponding to the major length and minor length of the ellipse and a relationship between an angle of an elliptical axis on the light receiving surface of the two-dimensional image pickup element 53 and the astigmatic axis are calibrated in advance in a process for manufacturing the apparatus.

The fixation guide lens 62 is moved to a position corresponding to the refractive power based on the obtained eye refractive power values by driving the fixation guide motor 65 through the motor driver 81. Therefore, the fixation chart 63 is exhibited to the eye to be examined E at a refractive power corresponding to the refractive power of the eye to be examined E. After that, the fixation guide lens 62 is moved away by the predetermined amount, thereby fogging the fixation chart 63. Then, the measurement light source 49 is turned on again and the refractive power is measured. Thus, the measurement of the refractive power and the fogging using the fixation chart 63 are repeated, so that a final measurement value of stable refractive power can be obtained.

In general, after that, the measurement of the refractive power is completed. Here, assume that the eye to be examined E has opacity resulting from cataract at the central region of the crystalline lens. In this case, even when the apparatus operates to perform the measurement based on the above-mentioned auto alignment at the same alignment position, the center of the eye to be examined E all the time, the projection light flux from the measurement light source 49 does not reach the eye fundus by the presence of the opacity. Therefore, an image of reflected light on the eye fundus is picked up by the two-dimensional image pickup element 58. As a result, even if the measurement is tried multiple times, the measurement cannot be completed because of the occurrence of error. In this embodiment, the mode of the apparatus is shifted to the following manual continuous measurement mode and the eye refractive power measurement based on manual alignment is performed on the eye to be examined E having the opacity.

(Manual Continuous Measurement)

When an error occurs during the eye refractive power measurement after the completion of the above-mentioned auto alignment, the mode of the apparatus is automatically shifted to the manual continuous measurement mode. In the manual continuous measurement mode, a measurement position of the measurement portion 3 is manually changed using the trackball 6 by the operator, thereby performing the measurement at a position which does not include the opacity. The turning on of the measurement light source 49, the light receiving in the two-dimensional image pickup element 58, the analysis of the picked up eye fundus image, and the calculation of the refractive power are repeated in succession.

During the manual continuous measurement mode, the operator operates the trackball 6 to perform the measurement while searching a measurable location in the pupil region of the eye to be examined E. When the central axis O of the measurement portion 3 is moved to a location which does not include the opacity of the eye to be examined E, the reflected light on the eye fundus can be received in the two-dimensional image pickup element 58, thereby calculating the eye refractive power. A measurement value is displayed on the display portion 1. When the measurement light flux is blocked by the opacity resulting from cataract and thus a light flux sufficient to calculate the measurement value cannot be received, an error message is displayed on the display portion 1.

According to the manual continuous measurement mode, the above-mentioned measurement operation is repeatedly performed until ten measurement values in total are obtained. When the ten measurement values are obtained, the measurement operations are stopped. Even when the number of measurement values is smaller than 10, the measurement operation is stopped immediately after the operation including the turning on of the measurement light source 49, the analysis of the eye fundus image, and the calculation is performed a predetermined number of times, for example, 40 times.

As other conditions for stopping an operation than this, a certain elapsed period from the time when the apparatus mode is shifted to the manual continuous measurement mode, for example, 45 seconds may be set as the time limit and, in the case where after a lapse of 45 seconds, the number of measurement values is smaller than 10, the operation may be stopped.

In the manual continuous measurement mode, the operator concentratedly searches the measurable location of the eye to be examined E. In the eye refractive power measuring apparatus according to this embodiment, the operator operates only the trackball 6. As described later, the alignment in the forward/backward direction (that is, focusing) and check of the alignment state are performed using the intervals between the cornea reflection bright spots Pr and Pl by the eye refractive power measuring apparatus.

As well known, an interval d between the cornea reflection bright spots Pr and Pl stored in the CPU 70 becomes shorter than d0 with increasing a distance between the eye to be examined E and the apparatus. The interval d becomes longer than d0 with reducing the distance between the eye to be examined E and the apparatus.

Figure 14:
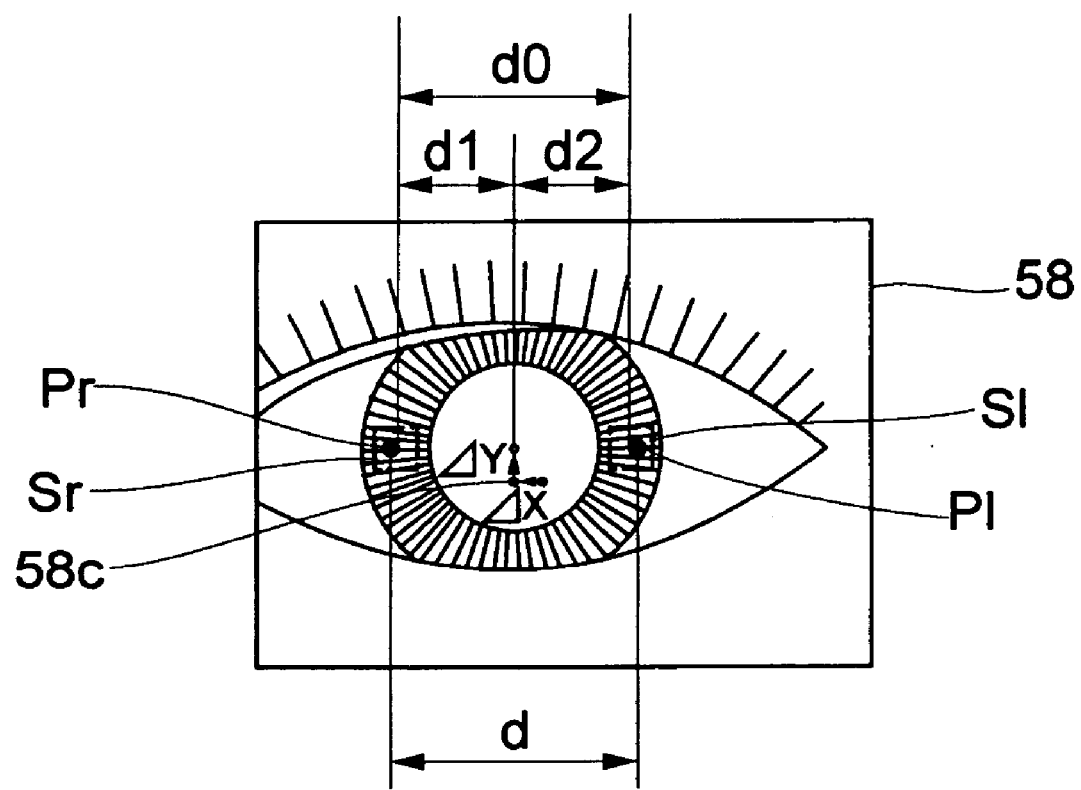
FIG. 14 is an explanatory view showing an anterior segment image.

Assume that the operator operates the trackball 6 to move the measurement portion 3 from a position at the time when the auto alignment is completed by Δx to the left and Δy in the up direction. In this case, as shown in FIG. 14, regarding areas for detecting the cornea reflection bright spots Pr and Pl, a position shifted from the center 58c of the sensor of the two-dimensional image pickup element 58 by Δx to the right and Δy in the up direction is set as the center. Scanning regions Sr and Sl located at distances of d1 and d2 from the center in the left/right direction are scanned to detect the cornea reflection bright spots Pr and Pl. Then, the interval d between the cornea reflection bright spots Pr and Pl is calculated.

When d>d0, the apparatus is brought closer to the eye to be examined E. Therefore, the forward/backward motor 32 is driven so as to bring the measurement portion 3 far from the eye to be examined E. On the other hand, when d<d0, the apparatus is brought far from the eye to be examined E. Therefore, the forward/backward motor 32 is driven so as to bring the measurement portion 3 closer to the eye to be examined E.

The CPU 70 controls the forward/backward motor 32 such that the interval d between the cornea reflection bright spots Pr and Pl becomes equal to d0. Alternatively, the CPU 70 controls the forward/backward motor 32 such that the interval d becomes substantially equal to d0 in view of an allowable error range in the forward/backward direction. Thus, the alignment state in the forward/backward direction can be maintained.

As described above, the scanning regions for the cornea reflection bright spots Pr and Pl are determined from the amount of operation of the trackball 6 and the interval d is calculated. Such checking and maintaining operation of the alignment state in the forward/backward direction is continuously performed while the operator operates the trackball 6 to perform the measurement and searches the measurement location in the manual continuous measurement mode.

Therefore, areas for detecting the cornea reflection bright spots Pr and Pl can be easily limited based on the amount of operation of the trackball 6. Thus, a load on the detection and alignment processing for a positional displacement in the forward/backward direction is small. Even when the measurement is successively performed, it is possible to perform the positional detection and alignment in the forward/backward direction during each measurement processing including the turning on of the measurement light source, the taking of the eye fundus image, and the calculation of the measurement values.

In this embodiment, while the manual continuous measurement is performed as described above, the apparatus checks the alignment state in the forward/backward direction. Here, assume that the apparatus mode is shifted to the manual continuous measurement mode in order to prevent the alignment position in the forward/backward direction from being significantly changed by careless contact of the operator with the roller 7. In this case, an operational instruction caused by the roller 7 is canceled out, so that the measurement portion 3 is prevented from being moved in the forward/backward direction by the operator. In order to allow the measurement portion 3 to operate in the forward/backward direction by the operator, the manual continuous measurement mode may be finished and shifted to a standby state for normal measurement. Alternatively, the measurement mode select switch 9 may be pressed to shift the apparatus mode to a manual measurement mode.

Figure 15:
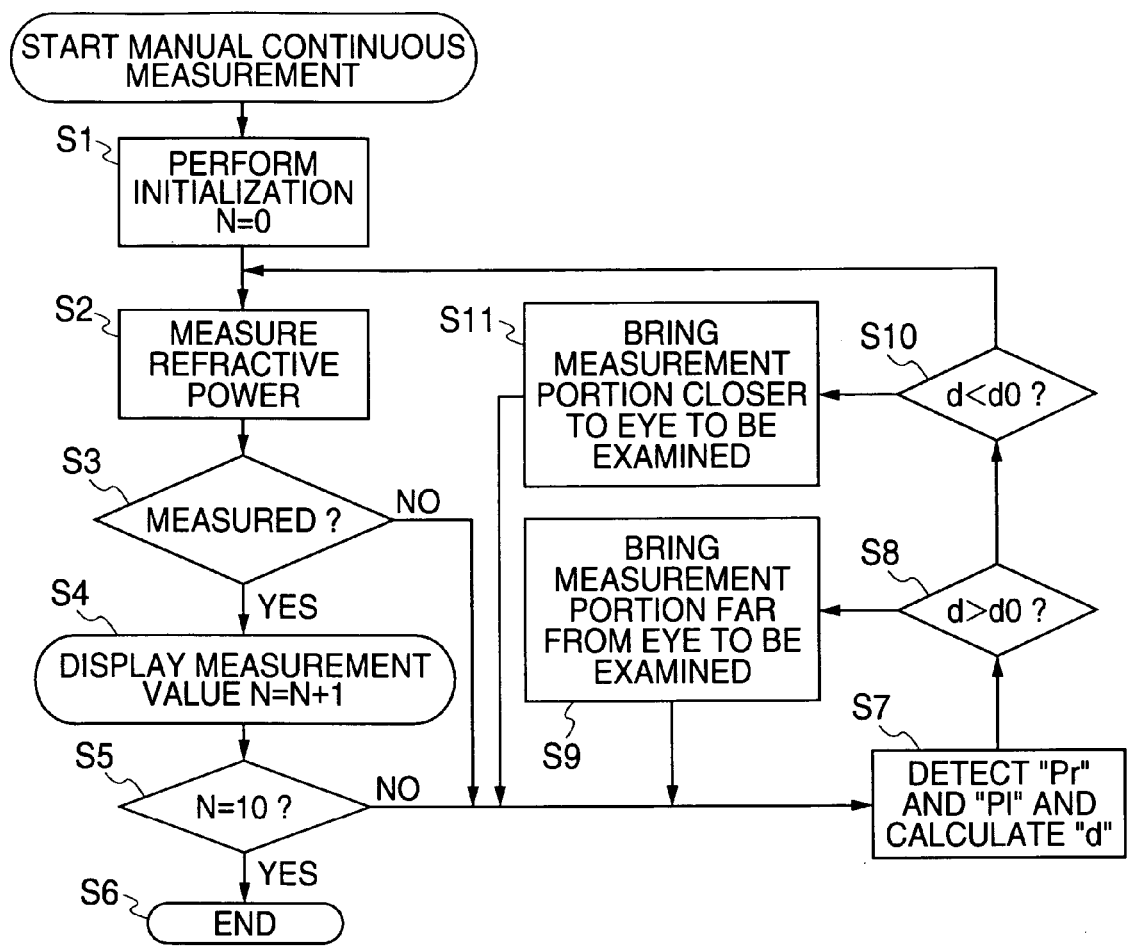
FIG. 15 is an operational flow chart showing manual continuous measurement.

FIG. 15 is an operational flow chart showing the above-mentioned manual continuous measurement according to this embodiment. When the apparatus mode is shifted to the manual continuous measurement mode, the number of measurement values obtained is initialized (Step S1) and the refractive power measurement operation is performed once (Step S2). Step S2 includes a step of turning on the measurement light source 49 and a step of analyzing the eye fundus image obtained from the two-dimensional image pickup element 53 to calculate the measurement values.

Whether a measurement value is obtained or an error occurs is determined (Step S3). When the measurement value is obtained, the number of measurement values (N) obtained is incremented by one (Step S4) and whether or not ten measurement values in total are obtained is checked (Step S5). When the number of measurement values (N) obtained reaches the predetermined number of measurement values (10), the measurement is ended (Step S6). When the number of measurement values (N) is smaller than 10, the flow of processing goes to Step S2 and the measurement operation is repeated.

In Step S3, when the measurement value is not obtained and the error occurs or when the number of measurement values (N) obtained is smaller than 10, the interval d between the cornea reflection bright spots Pr and Pl resulting from the anterior illumination light sources 60a and 60b is calculated (Step S7). When the interval d is larger than the initial value d0 (Step S8), the drive control is performed so as to bring the measurement portion 3 far from the eye to be examined E (Step S9). When the interval d is smaller than the initial value d0 (Step S10), the drive control is performed so as to bring the measurement portion 3 closer to the eye to be examined E (Step S11). Therefore, the alignment operation in the forward/backward direction is performed.

The operation for calculating the interval d0 between the bright spots Pr and Pl from the amount of operation of the trackball 6 and the amount of operation of the roller 7 is included in Step S7. While the alignment operation in the forward/backward direction is performed, the measurement and the check of the measurement values in Steps S2 to S5 are repeated for the continuous measurement.

Figure 16:
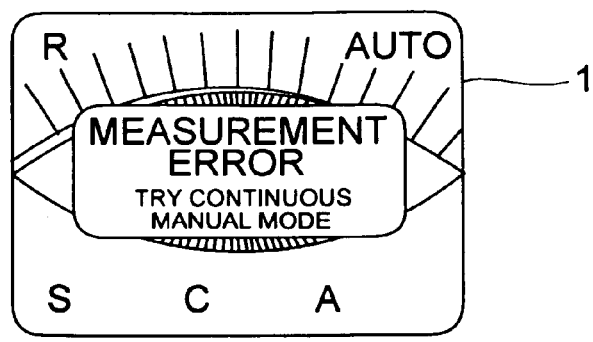
FIG. 16 is an explanatory view showing an error message displayed on a monitor screen.

In the example described in this embodiment, when an error occurs during the eye refractive power measurement after the completion of the auto alignment, the apparatus mode is automatically shifted to the manual continuous measurement mode. The following system can be also used. When a measurement error occurs as shown in FIG. 16, a message for recommending a shift to the manual continuous measurement mode to the operator is displayed on the display portion 1. For example, when the measurement mode select switch 9 is continuously pressed for several seconds, the system is shifted to the manual continuous measurement mode different from the normal manual measurement mode.

In the example described in this embodiment, the trackball 6 is used as means for performing operation in the left/right and up/down directions and the roller 7 is used as means for performing operation in the forward/backward direction. The present invention may be applied to an ophthalmologic apparatus having a structure in which the operation of, for example, a joystick is detected and the measurement portion 3 is electrically driven in the up/down, left/right, and forward/backward directions based on the detected amount of operation. Even when the apparatus mode is shifted to the manual continuous measurement mode and a drive instruction caused by the joystick in the forward/backward direction is prohibited to perform the auto alignment in the forward/backward direction while the continuous measurement is performed, the same effect can be obtained.

According to the ophthalmologic apparatus of this embodiment, the operation for searching the measurable location of the eye to be examined can be easily conducted without taking into consideration a positional displacement in the forward/backward direction.

Even when the operator carelessly touches second drive instruction means for instructing the drive in the forward/backward direction, the positional displacement in the forward/backward direction can be prevented.

When the auto alignment in the forward/backward direction is performed by alignment control means based on a positional relationship in the forward/backward direction, which is aligned by the second drive instruction means, the auto alignment in the forward/backward direction can be realized with high precision.

In general, the alignment and the measurement are performed in the auto alignment mode. Only when an error occurs, the apparatus is switched to the manual measurement mode. Thus, the present invention can be applied to any types of eyes to be examined.

As described above, according to the present invention, it is possible to provide an ophthalmologic apparatus which is easily operated.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2003-386995 filed on Nov. 17, 2003, which is hereby incorporated by reference herein.

What is claimed is:

1. An ophthalmologic apparatus comprising:
   a measurement portion adapted to measure an eye to be examined;
   an input device adapted to input information about an operation of a user;
   a detection device adapted to detect distances in up/down, left/right and forward/backward directions between the measurement portion and the eye;
   a drive device adapted to move the measurement portion in at least one of the up/down, left/right and forward/backward directions;
   a selection device adapted to select one of (1) a first mode in which the drive device is controlled to align the measurement portion with the eye with respect to the up/down, left/right and forward/backward directions on the basis of the distances in the up/down, left/right and forward/backward directions detected by the detection device, and (2) a second mode in which the drive device is controlled to align the measurement portion with the eye with respect to the forward/backward direction on the basis of the distance in the forward/backward direction detected by the detection device, and is controlled to move the measurement portion with respect to the up/down and left/right directions on the basis of information input from the input device; and
   a controller adapted to control the drive device in accordance with the mode selected by the selection device.

2. An ophthalmologic apparatus according to claim 1, wherein the detection device comprises:
   projection means for projecting an index to the eye to be examined;
   image pickup means for picking up an index image reflected by the eye to be examined; and
   calculation means for calculating the distance in the forward/backward direction between the measurement portion and the eye to be examined, on the basis of the picked up index image.

* * * * *

UNITED STATES PATENT AND TRADEMARK OFFICE
CERTIFICATE OF CORRECTION

PATENT NO. : 7,226,165 B2  Page 1 of 1
APPLICATION NO. : 10/968988
DATED : June 5, 2007
INVENTOR(S) : Yasuo Maeda It is certified that error appears in the above-identified patent and that said Letters Patent is hereby corrected as shown below:

IN THE DRAWINGS:
Sheet No. 4, Figure 7, "DIMENTIONAL" (both occurrences) should read --DIMENSIONAL--.

COLUMN 5:
Line 15, "pupil" should read --the pupil--.
Line 18, "pupil" should read --the pupil--.

COLUMN 8:
Line 28, "pupil." should read --the pupil.--.
Line 31, "pupil" should read --the pupil--.

Signed and Sealed this

Twentieth Day of May, 2008

JON W. DUDAS
*Director of the United States Patent and Trademark Office*